(12) United States Patent
Basset et al.

(10) Patent No.: US 7,635,794 B2
(45) Date of Patent: *Dec. 22, 2009

(54) METHOD FOR METATHESIS OF COMPOUNDS COMPRISING AN OLEFINIC DOUBLE BOND, IN PARTICULAR OLEFINS

(75) Inventors: Jean-Marie Basset, Caluire Et Cuire (FR); Jean Thivolle-Cazat, Fontaines sur Saone (FR); Mostafa Taoufik, Villeurbanne (FR); Erwan Le Roux, Bergen (NO); Christophe Coperet, Lyons (FR)

(73) Assignee: CPE Lyon Formation Continue ET Recherche-CPE Lyon FCR, Villeurbanne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/571,395

(22) PCT Filed: Jul. 1, 2005

(86) PCT No.: PCT/FR2005/001692

§ 371 (c)(1),
(2), (4) Date: Feb. 6, 2008

(87) PCT Pub. No.: WO2006/013263

PCT Pub. Date: Feb. 9, 2006

(65) Prior Publication Data

US 2008/0255328 A1  Oct. 16, 2008

(30) Foreign Application Priority Data

Jul. 2, 2004 (FR) .................................. 04 07396

(51) Int. Cl.
*C07C 6/04* (2006.01)

(52) U.S. Cl. ...................................... 585/646; 585/643
(58) Field of Classification Search ................. 585/643, 585/646
See application file for complete search history.

(56) References Cited

U.S. PATENT DOCUMENTS

| 3,634,538 A * | 1/1972 | Steffgen ....................... 585/644 |
| 3,865,751 A * | 2/1975 | Banks et al. ................. 502/251 |
| 6,229,060 B1 * | 5/2001 | Vidal et al. .................. 585/708 |
| 6,632,765 B1 * | 10/2003 | Chen ........................... 502/53 |
| 2002/0002317 A1 * | 1/2002 | Schwab et al. .............. 585/643 |

OTHER PUBLICATIONS

Levisalles et al, "Etudes sur le mecanisme de la metathese des olefins i", 1980, pp. 195-207, vol. 192, No. 2, J. Organometallic Chemistry, The Netherlands.
Wengrovius et al, "Multiple metal-carbon bonds. 25. Preparation and structure of tungsten neopentylidene hydride, neopentylidene carbonyl, and neopentylidene ethylene complexes", 1982, p. 1739-1740, vol. 104, No. 6, Journal of the American Chemical Society.

* cited by examiner

*Primary Examiner*—In Suk Bullock
(74) *Attorney, Agent, or Firm*—B. Aaron Schulman; Terry L. Wright; Stites & Harbison PLLC

(57) ABSTRACT

The invention relates to a method for metathesis of one or several reagents comprising a linear or branched hydrocarbon chain containing a double olefinic bond $Csp^2=Csp^2$ consisting in reacting said reagent or reagents with a supported metal compound comprising an aluminum oxide-based support to which a tungsten hydride is grafted. Typically, each said reagent or reagents comprises from 2 to 30 carbon atoms. The reagent can be embodied in the form of olefin. The inventive method can be used, for example for producing propylene from ethylene and butane.

26 Claims, No Drawings

METHOD FOR METATHESIS OF COMPOUNDS COMPRISING AN OLEFINIC DOUBLE BOND, IN PARTICULAR OLEFINS

The present invention relates to a process for the metathesis of one or more reactants comprising an olefinic structure.

The reaction for the metathesis of olefins was discovered approximately 40 years ago; it is a reversible transalkylidenation reaction, that is to say a reversible reaction for exchange of alkylidene groups within an olefin (self-metathesis) or a mixture of olefins (crossed metathesis); in some cases, these olefins can comprise functional groups. Equations (1) and (2) respectively represent the self-metathesis and crossed metathesis reactions:

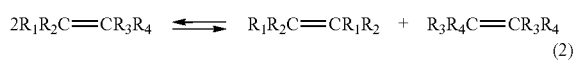
(1)

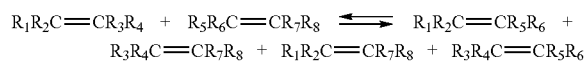
(2)

where $R_1$, $R_2$, $R_3$, $R_4$, $R_5$, $R_6$, $R_7$ and $R_8$ represent hydrogen atoms or functionalized or nonfunctionalized hydrocarbon groups.

The first catalysts described by Philips Petroleum, who discovered this reaction, were of heterogeneous type; they were composed essentially of $MoO_3$ deposited on silica or alumina, operating at approximately 150-200° C. but unstable and deactivating, or of $WO_3$ deposited on the same supports, operating at approximately 400-450° C.; the latter system, $WO_3/SiO_2$, remains the catalyst used industrially. The disadvantages of the latter system include the high temperatures, both for the reaction itself and for the regeneration of the catalyst.

It would be highly advantageous to have available a heterogeneous catalytic system effective in the meta-thesis of reactants comprising an olefinic structure, e.g. olefins, which is capable of operating at relatively low temperature and which can be regenerated at moderate temperature.

An objective of the invention is thus to provide an effective process for the metathesis of reactants comprising an olefinic structure, e.g. olefins, using a catalyst which is capable of operating at relatively low temperature.

Another objective of the invention is to provide such a process in which the catalyst can be regenerated at moderate temperature.

A subject matter of the present invention is thus a process for the metathesis of one or more, preferably one or two, reactants comprising a linear or branched hydrocarbon chain comprising an olefinic double bond $Csp^2=Csp^2$ (olefinic structure), in which this reactant or these reactants is/are brought into the presence of a supported metal compound comprising a support based on aluminum oxide to which a tungsten hydride is grafted.

The olefinic double bond is included in a linear or branched hydrocarbon chain of formula $R_1R_2C=CR_3R_4$ comprising an olefinic double bond $Csp^2=Csp^2$ and identical or different substituents $R_i$ (i=1 to 4) on these carbons.

According to one characteristic of the invention, each reactant comprises, in total, from 2 to 30 carbon atoms.

According to a first embodiment, the invention relates to the metathesis of one or more olefins or alkenes, namely unsaturated, linear or branched, acyclic hydrocarbon(s), comprising a $Csp^2=Csp^2$ double bond between two carbon atoms, of empirical formula $C_nH_{2n}$ and preferably with n an integer ranging from 2 to 30. The $R_i$ substituents can, for example, be of the hydrogen, methyl, ethyl, propyl or isopropyl, butyl, sec-butyl or isobutyl, or pentyl, sec-pentyl, isopentyl or neopentyl type.

According to a specific aspect of this embodiment, the invention relates to a process for the production of propylene in which ethylene and butene are reacted in the presence of the supported metal compound comprising a support based on aluminum oxide to which a tungsten hydride is grafted.

According to a second embodiment, the reactant or reactants comprise(s) identical or different $R_i$ substituents chosen from hydrogen atoms, saturated, linear or branched, hydrocarbon groups and saturated cyclic hydrocarbon groups which optionally carry hydrocarbon substituents and which can be connected to the $Csp^2$ carbon of the olefinic double bond either directly or via a saturated hydrocarbon chain. The cyclic $R_i$ hydrocarbon substituents can, for example, be of the cyclopropyl, cyclobutyl, cyclopentyl or cyclohexyl type and the like or of substituted cyclic type, such as methylcycloalkyl, ethylcycloalkyl, methylenecycloalkyl or of formula —$(CH_2)_n$-cycloalkyl. In addition to hydrogen, the other substituents optionally present can, for example, be of the methyl, ethyl, propyl or isopropyl, butyl, sec-butyl or isobutyl, or pentyl, sec-pentyl, isopentyl or neopentyl type.

According to a third embodiment, the reactant or reactants comprise(s) identical or different $R_i$ substituents chosen from hydrogen atoms, saturated, linear or branched, hydrocarbon groups and aromatic rings which optionally carry saturated hydrocarbon substituents and which can be connected to the $Csp^2$ carbon of the olefinic double bond either directly or via a saturated hydrocarbon chain. The $R_i$ substituents comprising aromatic rings can, for example, be of the phenyl, tolyl, benzyl, xylyl or biphenyl type or of formula —$(CH_2)_n$-aryl. In addition to hydrogen, the other substituents optionally present can, for example, be of the methyl, ethyl, propyl or isopropyl, butyl, sec-butyl or isobutyl, or pentyl, sec-pentyl, isopentyl or neopentyl type.

According to a fourth embodiment, different reactants chosen from those described in the preceding three series are reacted together.

The process of the invention can be carried out at a temperature ranging from 20 to 600° C. According to an advantageous characteristic of the invention, the process is carried out at a relatively low temperature ranging from 20 to 350° C., preferably from 50 to 300° C., better still from 80 to 200° C.

According to another characteristic, the process is carried out under an absolute pressure ranging from 0.01 to 8 MPa, preferably from 0.01 to 1 MPa, better still from 0.1 to 0.5 MPa.

The reactant or reactants can be made use of in the gaseous or liquid form.

The process can be carried out in the presence of hydrogen or of an agent which forms hydrogen in situ. Thus, the process can be carried out under a hydrogen partial pressure ranging from 0.001 to 0.1 MPa. Mention may be made, as agent which forms hydrogen in situ, of cyclic compounds, such as cyclohexane, decahydro-naphthalene and tetrahydronaphthalene.

According to an advantageous characteristic of the invention, the catalyst can be reactivated or regenerated by bringing into contact with hydrogen, in particular pure hydrogen or hydrogen diluted in a neutral gas. The regeneration can be carried out with a hydrogen pressure ranging from 0.01 to 10 MPa, preferably from 0.1 to 2 MPa. It is possible to proceed in the following way. The feeding of the reactor with reactant(s) is halted. Hydrogen is subsequently injected and a hydrogen pressure is maintained for a time sufficient to regenerate the catalyst. Before resuming the metathesis reaction, it is preferable to drive off the excess hydrogen by introducing a neutral gas, e.g. argon. The regeneration temperature is advantageously between 50 and 300° C., preferably between 80 and 200° C.

The process of the invention can be carried out batchwise in a static reactor. However, it is preferably carried out continuously in a dynamic reactor.

The term "tungsten hydride grafted to a support based on aluminum oxide" is understood to mean, generally, a tungsten atom bonded to at least one hydrogen atom and, in particular by at least one single bond, to said support.

The metal compound essentially comprises a tungsten hydride grafted to a support based on aluminum oxide. In this compound, the support can be any support based on aluminum oxide and more particularly any support where the aluminum oxide is accessible in particular at the surface of said support. Thus, the support can be chosen from supports relatively homogeneous in composition based on aluminum oxide, having in particular a composition based on aluminum oxide relatively homogeneous throughout the body of the support, that is to say from the core up to the surface of the support, and also from heterogeneous supports based on aluminum oxide comprising aluminum oxide essentially at the surface of the supports. In the case of a heterogeneous support, the support can comprise aluminum oxide deposited on, supported on or grafted to a mineral solid which can itself be a solid inorganic support, in particular chosen from metals, oxides or sulfides, and salts, for example from silica and metal oxides.

The support can have a specific surface (B.E.T.) chosen within a range extending from 0.1 to 1000 m$^2$/g, preferably from 0.5 to 800 m$^2$/g. The specific surface (B.E.T.) is measured according to the standard ISO 9277 (1995).

The support can in particular comprise aluminum oxide, mixed aluminum oxides or modified aluminum oxides, in particular modified by one or more elements from Groups 15 to 17 of the Periodic Table of the Elements (as defined by the IUPAC in 1991 in which the groups are numbered from 1 to 18 and which is found, for example, in "CRC Handbook of Chemistry and Physics", 76th edition (1995-1996), by David R. Lide, published by CRC Press Inc., USA).

The term "aluminum oxide" (also known as simple alumina) is understood to mean, generally, an aluminum oxide substantially devoid of any other oxide (or comprising less than 2% by weight of one or more other oxides present in the form of impurities). If it comprises more than 2% by weight of one or more other oxides, then it is generally convenient to regard the oxide as a mixed aluminum oxide, that is to say an aluminum oxide combined with at least one other oxide.

The support can preferably comprise aluminum oxide chosen from porous aluminas, nonporous aluminas and mesoporous aluminas.

Porous aluminas are often referred to as "activated aluminas" or "transition aluminas". They generally correspond to various partially hydroxylated aluminum oxides Al$_2$O$_3$. They are porous supports generally obtained by an "activation" treatment comprising in particular a heat (or dehydration) treatment of a precursor chosen from aluminum hydroxides, such as aluminum trihydroxides, hydroxides of aluminum oxide or gelatinous aluminum hydroxides. The activation treatment makes it possible to remove the water present in the precursor but also, in part, the hydroxyl groups, thus leaving behind a few residual hydroxyl groups and a specific porous structure. The surface of the porous aluminas generally comprises a complex mixture of aluminum and oxygen atoms and of hydroxide ions which combine according to specific crystalline forms and which in particular produce both acidic and basic sites. It is thus possible to choose, as solid support, a porous alumina from γ-alumina (gamma-alumina), η-alumina (eta-alumina), δ-alumina (delta-alumina), θ-alumina (theta-alumina), κ-alumina (kappa-alumina), ρ-alumina (rho-alumina) and χ-alumina (chi-alumina) and preferably from γ-alumina and η-alumina. These various crystalline forms depend essentially on the choice of the precursor and of the conditions of the activation treatment, in particular the temperature and the pressure. The activation treatment can be carried out, for example, under a stream of air or a stream of another gas, in particular inert gas, at a temperature which can be chosen within a range extending from 100 to 1000° C., preferably from 200 to 1000° C.

Use can also be made of porous aluminas or semiporous aluminas prepared by an activation treatment as described above, in particular at a temperature ranging from 600 to 1000° C. These porous or semiporous aluminas can comprise mixtures of porous aluminas in at least one of the crystalline forms described above, such as γ-alumina, η-alumina, δ-alumina, θ-alumina, κ-alumina, ρ-alumina or χ-alumina, with a nonporous alumina, in particular α-alumina, in particular in a proportion of 20 to 80% by weight.

Porous aluminas are generally thermal decomposition products of aluminum trihydroxides, hydroxides of aluminum oxide (or hydrates of aluminum oxide) and gelatinous aluminum hydroxides (or alumina gels).

Aluminum trihydroxides of general formula Al(OH)$_3$=Al$_2$O$_3$.3H$_2$O can exist in different crystalline forms, such as gibbsite or hydrargillite (α-Al(OH)$_3$), bayerite (β-Al(OH)$_3$) or nordstrandite. Aluminum trihydroxides can be obtained by precipitation from aluminum salts in generally alkaline solutions.

Hydroxides of aluminum oxide of general formula AlO(OH)=Al$_2$O$_3$.H$_2$O can also exist in different crystalline forms, such as diaspore (β-AlO(OH)) or boehmite (or α-AlO(OH)). Diaspore can occur in certain types of clay and of bauxite and can be synthesized by heat treatment of gibbsite at approximately 150° C. or by hydrothermal treatment of boehmite at 380° C. under a pressure of 50 MPa. Boehmite can be easily obtained by heating the gelatinous precipitate formed on treating solutions of aluminum salts under cold conditions with ammonia. Hydroxides of aluminum oxide can also be obtained by hydrolysis of aluminum alkoxides.

Gelatinous aluminum hydroxides (or alumina gels) are generally poly(aluminum hydroxide)s, in particular of general formula:

$$nAl(OH)_3 \cdot (n-1)H_2O \qquad (1)$$

in which n is a number varying from 1 to 8. Gelatinous aluminum hydroxides can be obtained by one of the processes chosen from the thermal decomposition of an aluminum salt, such as aluminum chloride, the electrolysis of aluminum salts, such as a mixture of aluminum sulfate and of alkali metal sulfate, the hydrolysis of aluminum alkoxides, such as aluminum methoxide, precipitation from aluminates, such as alkali metal or alkaline earth metal aluminates, and precipitation from aluminum salts, for example by bringing into contact aqueous solutions of Al$_2$(SO$_4$)$_3$ and of ammonia, or of NaAlO$_2$ and of an acid, or of NaAlO$_2$ and of Al$_2$(SO$_4$)$_3$, it being possible for the precipitates thus obtained to be subsequently subjected to aging and drying in order to remove the water. Gelatinous aluminum hydroxides generally exist in the form of an amorphous alumina gel, in particular in the form of a pseudoboehmite.

The porous aluminas can have a specific surface (B.E.T.) chosen within a range extending from 100 to 1000 m²/g, preferably from 300 to 1000 m²/g, in particular from 300 to 800 m²/g, especially from 300 to 600 m²/g. They can in addition exhibit a specific pore volume equal to or less than 1 cm³/g, preferably equal to or less than 0.9 cm³/g, in particular equal to or less than 0.6 cm³/g.

The support can also comprise nonporous aluminas, preferably α-alumina (alpha-alumina), generally known under the term of "calcined alumina". α-Alumina exists in the natural state under the term of "corundum". It can be synthesized generally by heat treatment or calcination of a precursor chosen in particular from aluminum salts, hydroxides of aluminum oxide, aluminum trihydroxides and aluminum oxides, such as γ-alumina, at a temperature of greater than 1000° C., preferably of greater than 1100° C. It can comprise impurities, such as other oxides, for example $Fe_2O_3$, $SiO_2$, $TiO_2$, CaO, $Na_2O$, $K_2O$, MgO, SrO, BaO and $Li_2O$, in proportions of less than 2%, preferably less than 1%, by weight. The nonporous aluminas, such as α-alumina, can have a specific surface (B.E.T.) chosen within a range extending from 0.1 to less than 300 m²/g, preferably from 0.5 to 300 m²/g, in particular from 0.5 to 250 m²/g.

The support can also comprise mesoporous aluminas having in particular a specific surface (B.E.T.) chosen within a range extending from 100 to 800 m²/g. The mesoporous aluminas generally have pores with a width ranging from 2 nm to 0.05 μm.

The support can also comprise mixed aluminum oxides. The term "mixed aluminum oxides" is understood to mean, generally, aluminum oxides combined with at least one other oxide in a proportion by weight preferably from 2 to less than 80%, in particular from 2 to less than 50%, especially from 2 to less than 40% or even from 2 to less than 30%. The other oxide or oxides can be oxides of the elements M chosen from the metals from Groups 1 to 13 and elements from Group 14, with the exception of carbon, of the Periodic Table of the Elements. More particularly, they can be oxides of the elements M chosen from alkali metals, alkaline earth metals, transition metals and elements from Groups 13 and 14 of said table, with the exception of carbon. The transition metals generally comprise the metals from Groups 3 to 11 of said table, in particular elements 21 to 29, 39 to 47 and 57 to 79 (including lanthanides) and the actinides. The other oxide or oxides of the elements M are preferably chosen from the transition metals from Groups 3 to 7, the lanthanides, the actinides and the elements from Groups 13 and 14 of said table, with the exception of carbon. More particularly, they can be chosen from silicon, boron, gallium, germanium, titanium, zirconium, cerium, vanadium, niobium, tantalum, chromium, molybdenum and tungsten oxides.

The mixed aluminum oxides can be chosen from anhydrous aluminates, from spinels and from aluminosilicates. In particular, the anhydrous aluminates can be chosen from anhydrous alkali metal aluminates, such as anhydrous lithium aluminate ($LiAlO_2$) or anhydrous sodium aluminate ($Na_2O.Al_2O_3$), and anhydrous alkaline earth metal aluminates, such as anhydrous tricalcium aluminate ($3CaO.Al_2O_3$) or anhydrous beryllium aluminate ($BeO.Al_2O_3$). The spinels can be chosen in particular from aluminum oxides combined with oxides of divalent metals and in particular from magnesium spinel ($MgAl_2O_4$), calcium spinel ($CaAl_2O_4$), zinc spinel ($ZnAl_2O_4$), manganese spinel ($MnAl_2O_4$), iron spinel ($FeAl_2O_4$) and cobalt spinel ($CoAl_2O_4$). The alumino-silicates can be chosen in particular from clays, talc, micas, feldspar, microporous aluminosilicates, in particular molecular sieves, and zeolites.

The support can also comprise modified aluminum oxides, in particular modified by one or more elements from Groups 15 to 17, preferably Groups 16 to 17, of the Periodic Table of the Elements, for example phosphorus, sulfur, fluorine or chlorine. The support can in particular comprise alumina superacids or aluminum oxides which are sulfated, sulfided, chlorinated or fluorinated.

The support can be a support homogeneous in composition, in particular throughout the body of the support. It can also be a heterogeneous support based on aluminum oxide, in which support the aluminum oxide, the mixed aluminum oxides or the modified aluminum oxides, as described above, are essentially positioned at the surface of the support and the core of the support is essentially composed of a mineral solid chosen in particular from metals, oxides or sulfides, and salts, such as silica or metal oxides. The heterogeneous support can be prepared by dispersing over, by precipitating on and/or by grafting to the mineral solid one of the precursors of the compounds based on aluminum oxide mentioned above. The precursors can in particular be chosen from aluminum hydroxides, in particular from aluminum trihydroxides, hydroxides of aluminum oxide and gelatinous aluminum hydroxides. Preference is given to gelatinous aluminum hydroxides, such as described above, known under the term of alumina gels or of amorphous aluminas. A heterogeneous support can be prepared in particular by employing such a precursor by way of a sol-gel or using an organo-metallic compound, which facilitates in particular the grafting to the mineral solid.

The compound according to the invention is generally provided in the form of particles which can have any shape and any size, in particular a mean size ranging from 10 nm to 5 mm, preferably from 20 nm to 4 mm. The particles of the support can be provided as is or can be shaped so as to have a specific shape, in particular a spherical, spheroidal, hemispherical, hemispheroidal, cylindrical or cubic shape or the shape of rings, pellets, disks or granules.

The compound according to the invention essentially comprises a tungsten hydride grafted to the support based on aluminum oxide. The degree of oxidation of the tungsten in the supported metal compound can have a value chosen within a range extending from 2 to 6, preferably from 4 to 6. The tungsten atom is bonded in particular to the solid support, in particular via at least one single bond. It can in addition be bonded to one or more hydrogen atoms via single bonds (W—H) and optionally to one or more hydrocarbon radicals R, in particular via carbon-tungsten single or multiple bonds. The number of hydrogen atoms bonded to a tungsten atom depends on the degree of oxidation of the tungsten, on the number of single bonds bonding said tungsten atom to the support and optionally on the number of single or multiple bonds bonding said tungsten atom to the hydrocarbon radical R. Thus, the number of hydrogen atoms bonded to a tungsten atom can be at least equal to 1 and at most equal to 5 and can preferably range from 1 to 4, preferably from 1 to 3. The term "grafting of the tungsten hydride to the solid support based on aluminum oxide" is understood to mean, generally, that the tungsten atom is bonded via at least one single bond to said support and more particularly via at least one single bond (W—OAl) to at least one oxygen atom of the aluminum oxide. The number of single bonds bonding the tungsten atom to the support, in particular via a single bond (W—OAl), depends on the degree of oxidation of the tungsten and on the number of the other bonds bonding the tungsten atom and is generally equal to 1, 2 or 3.

The tungsten atom of the compound according to the invention can optionally be bonded to one or more hydrocarbon radicals R via one or more carbon-tungsten single, double or triple bonds. The hydrocarbon radical or radicals R can be identical or different, saturated or unsaturated, hydrocarbon radicals comprising in particular from 1 to 20, preferably from 1 to 10, carbon atoms and optionally comprising silicon, in particular in an organosilane group. They can be chosen in particular from alicyclic or aliphatic, in particular linear or branched, alkyl radicals, for example alkyl, alkylidene or alkylidyne radicals, in particular from $C_1$ to $C_{10}$ radicals, from aryl radicals, in particular from $C_6$ to $C_{12}$ radicals, and from aralkyl, aralkylidene or aralkylidyne radicals, in particular from $C_7$ to $C_{14}$ radicals.

The tungsten atom of the grafted tungsten hydride can be bonded to the hydrocarbon radical R via one or more carbon-tungsten single, double or triple bonds. A carbon-tungsten single bond, in particular of σ type, may be concerned: in this case, the hydrocarbon radical R can be an alkyl radical, in particular a linear or branched alkyl radical, or an aryl radical, for example, the phenyl radical, or an aralkyl radical, for example the benzyl radical or the radical of formula $C_6H_5$—$CH_2$—$CH_2$—. The term "alkyl radical" is understood to mean, generally, a monovalent aliphatic radical originating from the removal of a hydrogen atom on a carbon atom of the molecule of an alkane or of an alkene or of an alkyne or even of an organosilane, for example a methyl ($CH_3$—), ethyl ($C_2H_5$—), propyl ($C_2H_5$—$CH_2$—), neopentyl (($CH_3)_3C$—$CH_2$—), allyl ($CH_2$=$CH$—$CH_2$—), alkynyl (R—C≡C—), in particular ethynyl (CH≡C—), or neosilyl (($CH_3)_3Si$—$CH_2$—) radical. The alkyl radical can, for example, be of formula R'—$CH_2$— where R' represents a linear or branched alkyl radical.

A carbon-tungsten double bond, in particular of π type, may also be concerned: in this case, the hydrocarbon radical R can be an alkylidene radical, in particular a linear or branched alkylidene radical, or an aralkylidene radical. The term "alkylidene radical" is understood to mean, generally, a divalent aliphatic radical originating from the removal of two hydrogen atoms on the same carbon atom of the molecule of an alkane or of an alkene or of an alkyne or even of an organosilane, for example a methylidene ($CH_2$=), ethylidene ($CH_3$—CH=), propylidene ($C_2H_5$—CH=), neopentylidene (($CH_3)_3C$—CH=) or allylidene ($CH_2$=CH—CH=) radical. The alkylidene radical can, for example, be of formula R'—CH= where R' represents a linear or branched alkyl radical. The term "aralkylidene radical" is understood to mean, generally, a divalent aliphatic radical originating from the removal of two hydrogen atoms on the same carbon of an alkyl, alkenyl or alkynyl radical connected to an aromatic group.

A carbon-tungsten triple bond may also be concerned: in this case, the hydrocarbon radical R can be an alkylidyne radical, in particular a linear or branched alkylidyne radical, or an aralkylidyne radical. The term "alkylidyne radical" is understood to mean, generally, a trivalent aliphatic radical originating from the removal of three hydrogen atoms on the same carbon atom of the molecule of an alkane or of an alkene or of an alkyne or even of an organosilane, for example an ethylidyne ($CH_3$—C≡), propylidyne ($C_2H_5$—C≡), neopentylidyne (($CH_3)_3C$—C≡) or allylidyne ($CH_2$=CH—C≡) radical. The alkylidyne radical can, for example, be of formula R'—C≡ where R' represents a linear or branched alkyl radical. The term "aralkylidyne radical" is understood to mean, generally, a trivalent aliphatic radical originating from the removal of three hydrogen atoms on the same carbon of an alkyl, alkenyl or alkynyl radical connected to an aromatic group.

More particularly, the hydrocarbon radical R can be chosen from the methyl, ethyl, n-propyl, isopropyl, n-butyl, isobutyl, neopentyl, allyl, neopentylidene, allylidene, neopentylidyne and neosilyl radicals.

The tungsten atom of the compound according to the invention can be complexed by one or more hydrocarbon ligands, in particular aromatic or carbonyl ligands.

The tungsten hydride grafted to the support based on aluminum oxide can be represented diagrammatically by the following formula:

(2)

in which W, Al, O and H respectively represent tungsten, aluminum, oxygen and hydrogen atoms, M represents an atom of one or more elements of another oxide, such as defined above, R represents a hydrocarbon radical, such as defined above, and x, y, w and z are integers, the sum (w+x+y+z) of which is equal to 2 to 6, and with x=1 to 3, y=1 to 5, w=0 to 4 and z=0 to 2. In the formula (2), the —(Al—O) and —(M—O) bonds represent one or more single or multiple bonds respectively connecting the aluminum atom and the atom M to one of the atomic constituents of the support based on aluminum oxide, in particular to one of the oxygen atoms of this support.

The compound according to the invention generally exhibits, by infrared spectroscopy, one or more specific absorption bands of the W—H bond, the frequency of which bands can vary according to the coordination sphere of the tungsten and can depend in particular on the number of bonds of the tungsten with the support, with the hydrocarbon radicals R and with other hydrogen atoms. Thus, for example, at least two absorption bands at 1903 and 1804 cm$^{-1}$ have been found, which bands are specific in particular of the W—H bond considered in particular in the environment of the W—OAl bonds bonding the same tungsten atom to an oxygen atom itself bonded to an aluminum atom of α-alumina. By way of comparison, tungsten hydride grafted under the same conditions to a silica support generally exhibits, by infrared spectroscopy, at least one of the two absorption bands at 1940 and 1960 cm$^{-1}$, which bands are different from the above and which are in particular specific of the W—H bond considered in particular in the environment of the W—OSi bonds bonding the same tungsten atom to an oxygen atom itself bonded to a silicon atom of the silica support.

Another way of being able to characterize the presence of a W—H bond in the compound according to the invention comes from a measurement by proton Nuclear Magnetic Resonance (solid $^1$H NMR) at 500 MHz, where the value of the chemical shift of the tungsten hydride ($\delta_{W-H}$) is equal to 10.6 ppm (parts per million).

The compound according to the invention can additionally comprise an aluminum hydride, in particular at the surface of the support and in particular in the vicinity of the grafted tungsten hydride. It is believed that an aluminum hydride can be formed by opening of an aluminoxane bridge (of formula Al—O—Al) present in particular at the surface of the support and by reaction between a hydrogen atom of a grafted tungsten hydride and the aluminoxane bridge thus opened. A simple test for the characterization of the aluminum hydride present in the compound of the invention next to a tungsten hydride comprises a reaction for the deuteration of said compound. The test can be carried out by bringing the compound according to the invention into contact with a deuterium atmosphere under an absolute pressure of 66.7 kPa, at a temperature chosen between 25 and 80° C., preferably equal to 60° C., for a period of time of 15 minutes. A selective deuteration reaction is thus carried out under these conditions: it makes it possible to substitute the hydrogen atoms by deuterium atoms in the W—H bonds and to thus form new W-D bonds which, by infrared spectroscopy, exhibit two absorption bands at 1293 and 1393 $cm^{-1}$, while leaving unchanged the hydrogen atoms in the Al—H bonds which can then be characterized, by infrared spectroscopy, by an absorption band at 1914 $cm^{-1}$.

The present invention also relates to a process for the preparation of the supported metal compound. The compound according to the invention, which exists essentially in the form of a tungsten hydride grafted to a support based on aluminum oxide, can be prepared by a process comprising the following stages:

(1) a stage in which an organometallic tungsten precursor (Pr) is dispersed over and grafted to a support based on aluminum oxide, in which precursor the tungsten is in particular bonded or complexed to at least one hydrocarbon ligand, so as to form a tungsten hydrocarbon compound or complex grafted to said support, then (2) a stage of hydrogenolysis of the grafted tungsten hydrocarbon compound or complex resulting from the preceding stage, so as to form a tungsten hydride grafted to said support.

The organometallic tungsten precursor Pr preferably comprises a tungsten atom bonded or complexed to one or more hydrocarbon ligands. The tungsten atom can in particular be bonded to a carbon of the hydrocarbon ligand via carbon-tungsten single, double or triple bonds. The hydrocarbon ligands can be identical or different, saturated or unsaturated, hydrocarbon radicals, in particular aliphatic or alicyclic hydrocarbon radicals, preferably $C_1$ to $C_{20}$ radicals, in particular $C_1$ to $C_{10}$ radicals, and can be chosen in particular from the hydrocarbon radicals R described above. The number of hydrocarbon ligands bonded to the tungsten atom depends on the degree of oxidation of the tungsten in the precursor Pr and can be at most equal to the degree of oxidation of the tungsten in the precursor Pr, in particular be greater than 0 and at most equal to the maximum degree of oxidation of the tungsten and preferably have any value ranging from 2 to 6, in particular from 4 to 6.

The precursor Pr can comprise a tungsten atom in particular complexed to one or more hydrocarbon ligands such that the degree of oxidation of the tungsten is equal to 0. The hydrocarbon ligand can be chosen from aromatic ligands or carbonyl ligands. Thus, the precursor Pr can be chosen from tungsten bisarene and tungsten hexacarbonyl.

Prior to the first dispersing and grafting stage, the support based on aluminum oxide can be subjected to a preliminary stage of calcination and/or of dehydroxylation. The support can be calcined so as to oxidize the carbon possibly present in the support and to remove it in the form of carbon dioxide. The calcination can be carried out by subjecting the support to an oxidizing heat treatment, in particular under a stream of dry air, at a temperature lower than the sintering temperature of the support, for example at a temperature ranging from 100 to 1000° C., preferably from 200 to 800° C., for a sufficient period of time which makes it possible to remove the carbon dioxide and which can range from 0.1 to 48 hours, under a pressure of less than, equal to or greater than atmospheric pressure.

The support can also be subjected to another preliminary stage, referred to as dehydroxylation. This stage can be carried out so as to optionally remove the residual water from the support and a portion of the hydroxyl groups, to leave behind, in particular at the surface of the support, a residual amount of the hydroxyl groups and to optionally form aluminoxane bridges (of formula Al—O—Al). The dehydroxylation can be carried out by subjecting the support to a heat treatment under an inert gas stream, for example under a stream of nitrogen, of argon or of helium, under a pressure preferably of less than atmospheric pressure, for example under an absolute pressure ranging from $10^{-4}$ Pa to $10^2$ kPa, preferably from $10^{-2}$ Pa to 50 kPa, at a temperature of less than the sintering temperature of the support, for example at a temperature ranging from 100 to 1000° C., preferably from 200 to 800° C., and for a sufficient period of time which makes it possible to leave an appropriate residual amount of hydroxyl and/or aluminoxane groups in the support and which can range from 0.1 to 48 hours. The dehydroxylation stage can advantageously be carried out after the calcination stage.

The dispersing and grafting stage can be carried out by sublimation, by impregnation using a solvent or by dry mixing. In the case of a stage by sublimation, the precursor Pr, which generally exists in the solid state under standard conditions, is heated, in particular under a pressure of less than atmospheric pressure and under temperature conditions which provide for its sublimation and its migration in the gaseous state over the support. The sublimation can be carried out at a temperature ranging from −30 to 200° C. and in particular under an absolute pressure ranging from $10^{-4}$ to 1 Pa. The grafting of the precursor Pr to the support can be monitored by infrared spectroscopy. The excess precursor Pr which has not grafted to the support can be removed by reverse sublimation.

The dispersing and grafting stage can also be carried out by impregnation using a solvent. In this case, the precursor Pr can be dissolved in a polar or nonpolar organic solvent, for example pentane or ethyl ether. The impregnation can be carried out by bringing the support based on aluminum oxide into contact with the solution, prepared beforehand, of the precursor Pr. The impregnation can be carried out at a temperature ranging from −80 to 200° C., under an inert atmosphere, for example an atmosphere of nitrogen, of argon or of helium, and preferably with stirring. A suspension of a tungsten hydrocarbon compound or complex grafted to the support is thus obtained. The excess precursor Pr which has not grafted to the support can be removed by washing using an organic solvent identical to or different from that used during the impregnation.

The dispersing and grafting stage can also be carried out by dry mixing, in particular by dry mechanical mixing, in the absence of liquid or of liquid solvent. In this case, the precursor Pr, which is present in the form of a solid, is mixed with the support based on aluminum oxide in the absence of liquid or of liquid solvent, in particular with mechanical stirring and under an inert atmosphere, for example an atmosphere of nitrogen, of argon or of helium, so as to form a mixture of two solids. During or after the dry mixing, it is possible to carry out a heat treatment and/or a treatment under a pressure of less than atmospheric pressure, so as to bring about the migration and the reaction of the precursor Pr with the support. The precursor which has not been grafted to the support can be removed by reverse sublimation or by washing using an organic solvent.

The preparation of the compound according to the invention can comprise a second stage referred to as hydrogenolysis. It is a reaction for the hydrogenolysis of the tungsten hydrocarbon compound or complex grafted to the support as prepared in the preceding stage. The reaction is generally carried out so as to form a tungsten hydride grafted to the support. The term "hydrogenolysis" is understood to mean, generally, a reaction in which a molecule is cleaved with attachment of hydrogen to the two cleaved portions. To be specific, the cleavage reaction takes place in particular between the tungsten atom grafted to the support and the carbon atom of the precursor Pr attached to or complexed with said tungsten atom. The hydrogenolysis can be carried out using hydrogen or a reducing agent capable in particular of converting the grafted tungsten hydrocarbon compound or complex to grafted tungsten hydride. The hydrogenolysis can be carried out by bringing the grafted tungsten hydrocarbon compound or complex into contact with hydrogen or the reducing agent. It can be carried out under a hydrogen atmosphere or an inert atmosphere, when a reducing agent is used, under an absolute pressure ranging from $10^{-2}$ to 10 MPa, at a temperature ranging from 20 to 500° C., for a period of time ranging from 0.1 to 48 hours.

The present invention furthermore relates to the use of the supported metal compound according to the invention and as disclosed in FR 03 03588 in a process employing cleavage and recombination reactions of $Csp^2=Csp^2$ olefinic double bonds to manufacture novel olefins. It relates more particularly to the use of the compound according to the invention as catalyst in reactions for the metathesis of an olefin with itself (self-metathesis) or with at least one other olefin (crossed metathesis) as represented in the above equations (1) and (2).

The following examples illustrate the present invention.

EXAMPLE 1

Preparation of a Tungsten Hydride Grafted to an Alumina

In a preliminary stage, 530 mg of a γ-alumina, having a mean size of 40 μm and a specific surface (B.E.T.) of 200 m$^2$/g, comprising 90% by weight of alumina and 9% by weight of water and sold by Johnson Matthey (Great Britain), are subjected to a calcination treatment under a stream of dry air at 500° C. for 15 hours and then to a dehydroxylation treatment under an absolute pressure of $10^{-2}$ Pa at 500° C. for 15 hours, so that the alumina thus calcined and dehydroxylated exhibits, by infrared spectroscopy, three absorption bands respectively at 3774, 3727 and 3683 cm$^{-1}$ characteristic in particular of residual AlO—H bond.

In a first stage, the 530 mg of the alumina prepared above are introduced into a glass reactor under an argon atmosphere and at 25° C., followed by a solution of 6 ml of n-pentane comprising 300 mg of tris(neopentyl)neopentylidynetungsten, used as precursor Pr and corresponding to the general formula:

$$W[-CH_2-C(CH_3)_3]_3[\equiv C-C(CH_3)_3] \qquad (3)$$

The mixture thus obtained is maintained at 25° C. for 3 hours. At the end of this time, a tungsten organometallic compound grafted to the alumina is obtained, the excess precursor Pr which has not reacted being removed by washing with n-pentane at 25° C. The tungsten organometallic compound thus grafted is dried under vacuum. It comprises 1.5% by weight of tungsten and corresponds to the general formula:

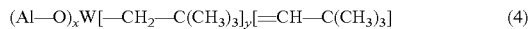

$$(Al-O)_xW[-CH_2-C(CH_3)_3]_y[\equiv CH-C(CH_3)_3] \qquad (4)$$

with x=1 and y=2.

In a second stage, 50 mg of the grafted tungsten organometallic compound obtained above are isolated and subjected in a glass reactor to a hydrogenolysis treatment by bringing into contact with hydrogen under an absolute hydrogen pressure of 73 kPa at 150° C. for 15 hours. At the end of this time, the reactor is cooled to 25° C. and a compound (W/Al-1) according to the invention, which comprises in particular a tungsten hydride grafted to the alumina, is obtained and isolated under argon. The compound (W/Al-1) comprises 1.5% by weight of tungsten and exhibits, by infrared spectroscopy, two absorption bands respectively at 1903 and 1804 cm$^{-1}$ characteristic of the W—H bond grafted in particular to the alumina.

EXAMPLE 2

Preparation of a Tungsten Hydride Grafted to an Alumina

The preliminary stages of calcination and of dehydroxylation of the α-alumina are absolutely identical to those of example 1.

In a first stage, 53 mg of the alumina prepared above are isolated and introduced into a glass reactor at 25° C. under an argon atmosphere. The precursor Pr of general formula (3) as used in example 1 is then introduced into the reactor. The reactor is then heated at 70° C. for 2 hours, so as to sublime the precursor Pr over the alumina and to form a tungsten organometallic compound grafted to the alumina. At the end of this time, the excess precursor Pr which has not reacted is removed by reverse sublimation at 70° C. Subsequently, the reactor is cooled to 25° C. and a tungsten organo-metallic compound thus grafted which comprises 3.7% by weight of tungsten and which corresponds to the preceding general formula (4) is isolated under argon.

The second stage is carried out exactly as in example 1, except for the fact that use is made of the tungsten organometallic compound grafted to the alumina prepared in the preceding stage. A compound (W/Al-2) according to the invention comprising a tungsten hydride grafted to the alumina and comprising 3.7% by weight of tungsten is thus obtained. It exhibits, by infrared spectroscopy, two absorption bands respectively at 1903 and 1804 cm$^{-1}$ characteristic of the W—H bond grafted in particular to the alumina.

The compound (W/Al-2) is subjected to a selective deuteration test which shows that it comprises a tungsten hydride and an aluminum hydride, both grafted to the alumina. A sample of the compound (W/Al-2) is placed in a glass reactor and is then brought into contact, in this reactor, with a deuterium atmosphere under an absolute pressure of 66.7 kPa at a temperature of 60° C. for 15 minutes. At the end of this time, the reactor is cooled to 25° C. and the solid compound thus deuterated is isolated under argon; this compound exhibits, by infrared spectroscopy, an absorption band at 1914 cm$^{-1}$ characteristic of the Al—H bond unchanged by the deuteration reaction carried out under these conditions. Furthermore, it is observed that the absorption bands at 1903 and 1804 cm$^{-1}$ characteristic of the W—H bond grafted to the alumina disappear to the advantage of the absorption bands respectively at 1293 and 1393 cm$^{-1}$ characteristic of the W-D bond grafted to the alumina and formed by the deuteration reaction of the W—H bonds.

EXAMPLE 3

Preparation of a Tungsten Hydride Grafted to an Alumina

The preliminary stages of calcination and of dehydroxylation of the alumina are absolutely identical to those described in example 1.

In a first stage, 2 g of the alumina prepared above are isolated and introduced under an argon atmosphere into a glass reactor at 25° C. equipped with a magnetic stirring bar. 305 mg of the precursor Pr of general formula (3) as used in example 1 are then introduced into the reactor. The reactor is heated to 66° C. and the dry mixture thus prepared is stirred for 4 hours. At the end of this time, the reactor is cooled to 25° C. and then the solid mixture is washed with n-pentane at 25° C. The solid compound thus washed is dried under vacuum and then isolated under argon, so as to obtain a tungsten organometallic compound grafted to the alumina comprising 3.9% by weight of tungsten and corresponding to the preceding general formula (4).

The second stage is carried out exactly as in example 1, except for the fact that use is made of the tungsten organometallic compound grafted to the alumina prepared above. A compound (W/Al-3) according to the invention comprising a tungsten hydride grafted to the alumina and comprising 3.9% by weight of tungsten is thus obtained. It exhibits, by infrared spectroscopy, two absorption bands respectively at 1903 and 1804 cm$^{-1}$ characteristic of the W—H bond grafted to the alumina. Furthermore, it exhibits, by nuclear magnetic resonance (solid $^1$H NMR) at 500 MHz, a value of the chemical shift of the tungsten hydride ($\delta_{W-H}$) equal to 10.6 ppm (parts per million).

EXAMPLE 4

Preparation of a Tungsten Hydride Grafted to a Silica/Alumina

In a preliminary stage, 530 mg of a silica/alumina, having a specific surface (B.E.T.) of 475 m$^2$/g, comprising 33% by weight of alumina and sold by Akzo Nobel, are subjected to a calcination treatment under a stream of dry air at 500° C. for 15 hours and then to a dehydroxylation treatment under an absolute pressure of 10$^{-2}$ Pa at 500° C. for 15 hours, so that the silica/alumina thus calcined and dehydroxylated exhibits, by infrared spectroscopy, an absorption band at 3747 cm$^{-1}$ characteristic in particular of residual SiO—H bond.

In a first stage, the 530 mg of silica/alumina prepared above are introduced into a glass reactor under an argon atmosphere and at 25° C., followed by a solution of 6 ml of n-pentane comprising 300 mg of the precursor Pr of general formula (3) as used in example 1.

The mixture thus obtained is maintained at 25° C. for 3 hours. At the end of this time, a tungsten organo-metallic compound grafted to the silica/alumina is obtained, the excess precursor Pr which has not reacted being removed by washing with n-pentane at 25° C. The tungsten organometallic compound thus grafted is dried under vacuum. It comprises 1.5% by weight of tungsten and corresponds to the general formula:

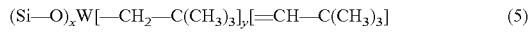

(Si—O)$_x$W[—CH$_2$—C(CH$_3$)$_3$]$_y$[=CH—C(CH$_3$)$_3$]     (5)

with x=1 and y=2.

In a second stage, 50 mg of the grafted tungsten organometallic compound obtained above are isolated and are subjected, in a glass reactor, to a hydrogenolysis treatment by bringing into contact with hydrogen under an absolute hydrogen pressure of 73 kPa at 150° C. for 15 hours. At the end of this time, the reactor is cooled to 25° C. and a compound (W/SiAl-1) according to the invention which comprises in particular a tungsten hydride grafted to silica/alumina is obtained and isolated under argon. The compound (W/SiAl-1) comprises 1.5% by weight of tungsten and exhibits, by infrared spectroscopy, two absorption bands respectively at 1906 and 1804 cm$^{-1}$ characteristic of the W—H bond grafted in particular to silica/alumina.

EXAMPLE 5

Preparation of a Tungsten Hydride Grafted to a Silica/Alumina

The preliminary stages of calcination and of dehydroxylation of the silica/alumina are absolutely identical to those described in example 3.

In a first stage, 1 g of the silica/alumina prepared above is isolated and introduced under an argon atmosphere into a glass reactor at 25° C. equipped with a magnetic stirring bar. 305 mg of the precursor Pr of general formula (3) as used in example 1 are then introduced into the reactor. The reactor is heated at 66° C. and the dry mixture thus produced is stirred for 4 hours. At the end of this time, the reactor is cooled to 25° C. and then the solid mixture is washed with n-pentane at 25° C. The solid compound thus washed is dried under vacuum and then isolated under argon, so as to obtain a tungsten organometallic compound grafted to the silica/alumina comprising 7.5% by weight of tungsten and corresponding to the preceding general formula (5).

The second stage is carried out exactly as in example 1, except for the fact that use is made of the tungsten organometallic compound grafted to the silica/alumina prepared above. A compound (W/SiAl-2) according to the invention comprising a tungsten hydride grafted to the silica/alumina and comprising 7.5% by weight of tungsten is thus obtained. It exhibits, by infrared spectroscopy, two absorption bands respectively at 1903 and 1804 cm$^{-1}$ characteristic of the W—H bond grafted to the silica/alumina. Furthermore, it exhibits, by nuclear magnetic resonance (solid $^1$H NMR) at 500 MHz, a value of the chemical shift of the tungsten hydride ($\delta_{W-H}$) equal to 10.6 ppm (parts per million).

EXAMPLE 6

Reaction for the Metathesis of Propene Catalyzed by W/Al-3 in a Static Reactor The supported metal compound (W/Al-3) prepared according to example 3 is used in a reaction for the metathesis of propene which can be represented by the following equation:

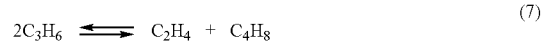

$$2C_3H_6 \rightleftharpoons C_2H_4 + C_4H_8 \tag{7}$$

The experiment is carried out in the following way: the supported metal compound is prepared "in situ" in a glass reactor as described in example 3. The reactor is subsequently placed under vacuum, then filled with propene up to a pressure of 76 kPa and, finally, heated at 150° C. The formation is then observed of a mixture essentially of ethylene, of n- and isobutenes, and also of pentenes and hexenes in smaller amounts, which are analyzed and quantitatively determined by gas chromatography (capillary column KCl/Al$_2$O$_3$, 50 m×0.32 mm; detection by flame ionization).

The cumulative conversion of propene, which is the number of moles of propene converted with respect to the number of moles of propene introduced initially, and the number of rotations (T.O.N.) or cumulative number of moles of propene converted over time per mol of tungsten of the supported metal compound are calculated.

The selectivities (SC$_2$), (SC$_4$), (SC$_5$) and (SC6) for the various products are also calculated respectively according to the following equations:

SC$_2$=(number of moles of ethylene formed)/(total number of moles of olefins formed)

SC$_4$=(number of moles of n-butenes formed)/(total number of moles of olefins formed)

SC$_5$=(number of moles of pentenes formed)/(total number of moles of olefins formed)

SC6=(number of moles of hexenes formed)/(total number of moles of olefins formed)

The results of the measurements and calculations defined above for the reaction for the metathesis of propene as a function of the time are collated in table 1 below.

| Time (h) | Cumulative conversion (%) | T.O.N. | Selectivities of the products formed (%) | | | |
|---|---|---|---|---|---|---|
| | | | SC$_2$ ethylene (%) | SC$_4$ butenes (%) | SC$_5$ pentenes (%) | SC$_6$ hexenes (%) |
| 0 | 0 | 0 | 0 | 0 | 0 | 0 |
| 0.33 | 32.8 | 481 | 50.6 | 47.3 | 1.87 | 0.23 |
| 0.75 | 38.43 | 565 | 51.88 | 45.6 | 2.21 | 0.28 |
| 1.33 | 41.26 | 600.6 | 49.46 | 47.37 | 2.92 | 0.43 |
| 2 | 41.8 | 605.6 | 48.5 | 47.76 | 3.24 | 0.62 |
| 3 | 42.5 | 611 | 46.75 | 49.33 | 3.3 | 0.62 |

Metathesis of propene in a static reactor catalyzed by WH/α-alumina (W/Al-3) at 150° C.; M cat=50 mg (% W=3.86%), V reactor=505 ml, P propene=76 kPa Propene/Ws=1470

EXAMPLE 7

Reaction for the Metathesis of Propene Catalyzed by W/Al-3 in a Static Reactor

The experiment is carried out in a similar way to example 6, except that the reaction is carried out at 80° C.

The results of the measurements and calculations as defined in example 6 for the reaction for the metathesis of propene as a function of the time are collated in table 2 below.

| Time (h) | Cumulative conversion (%) | T.O.N. | Selectivities of the products formed (%) | | | |
|---|---|---|---|---|---|---|
| | | | SC$_2$ ethylene (%) | SC$_4$ butenes (%) | SC$_5$ pentenes (%) | SC$_6$ hexenes (%) |
| 0.25 | 14.96 | 219 | 53.09 | 46.91 | 0 | 0 |
| 0.5 | 20.07 | 294 | 51.61 | 48.39 | 0 | 0 |
| 1 | 23.56 | 346 | 53.39 | 46.61 | 0 | 0 |
| 2 | 27.53 | 404 | 52.65 | 47.35 | 0 | 0 |

EXAMPLE 8

Reaction for the Metathesis of Propene Catalyzed by W/Al-3 in a Dynamic Reactor

The complex (Al—O)$_x$W[—CH$_2$—C(CH$_3$)$_3$]$_y$[=CH—C(CH$_3$)$_3$] (4) grafted to the alumina by sublimation (200 mg; 3.86% W/Al$_2$O$_3$; 42 micromol of W) according to example 3 is transferred in a glove box into a tubular stainless steel reactor which can be isolated from the atmosphere. After connecting the reactor to the assembly, the circuit is purged with argon and then the supported tungsten hydride catalyst [W]$_s$—H is prepared in situ by treatment of the grafted alkyl-alkylidyne complexes under a stream of hydrogen (3 ml/min) at 150° C. for 15 h, resulting in the compound (W/Al-3). After cooling to 25° C., the reactor is purged of the excess hydrogen with argon and then under a stream of propene at 101.3 kPa (5 ml/min, i.e. a molar flow rate of 5.31 propene/W/min). The reactor is then rapidly brought to the temperature of 150° C. (rise of 250° C./h). The products are analyzed on line by gas chromatography (capillary column KCl/Al$_2$O$_3$, 50 m×0.32 mm; detection by flame ionization). The formation is then observed mainly of ethylene, of butenes, of pentenes and of hexenes in small amounts.

The results of the measurements and calculations as defined in example 6 for the reaction for the metathesis of propene as a function of the time are collated in table 3 below. In this case, an instantaneous conversion, which is the number of moles of propene converted with respect to the number of moles of propene introduced at each instant, is defined.

| Time (h) | Instantaneous conversion (%) | Cumulative T.O.N. | Molar composition of the gas phase in % | | | | | |
|---|---|---|---|---|---|---|---|---|
| | | | SC$_2$ ethylene (%) | SC$_3$ propylene (%) | SC$_4$ butenes (%) | SC$_5$ pentenes (%) | SC$_6$ hexenes (%) | SC$_7$ heptenes (%) |
| 0 | 0 | 0 | 0 | 0 | 0 | 0 | 0 | 0 |
| 14 | 40 | 1784 | 18.5 | 60 | 19.6 | 1.44 | 0.4 | 0.07 |
| 31 | 39.3 | 3950 | 18.6 | 60.7 | 19 | 1.25 | 0.33 | 0.06 |
| 48 | 38.7 | 6117 | 18.6 | 61.3 | 18.7 | 1.15 | 0.28 | 0.05 |
| 65 | 38.4 | 8283 | 18.5 | 61.6 | 18.4 | 1.07 | 0.26 | 0.046 |
| 114 | 37.5 | 14528 | 18.31 | 62.5 | 18 | 0.93 | 0.21 | 0.037 |
| 148 | 37.7 | 18861 | 18.1 | 62.3 | 18.5 | 0.87 | 0.2 | 0.033 |
| 182 | 36.44 | 23194 | 18 | 63.56 | 17.4 | 0.82 | 0.18 | 0.031 |
| 203 | 36.24 | 25870 | 17.95 | 63.76 | 17.28 | 0.79 | 0.17 | 0.029 |
| 213 | 36.1 | 27144 | 17.87 | 63.9 | 17.2 | 0.78 | 0.17 | 0.029 |

EXAMPLE 9

Ethylene/2-Butene Crossed Metathesis Reaction Catalyzed by W/Al-3 in a Static Reactor The experiment is carried out in a similar way to example 6, except that the reaction is carried out at 150° C. with a 50/50 molar mixture of ethylene and of 2-butene instead of propene. Propene is then mainly formed according to the reaction:

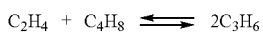

The results of the measurements and calculations as defined in example 6 for the ethylene/2-butene crossed metathesis reaction as a function of the time are collated in table 4 below.

| Time (h) | Molar composition of the gas phase (%) | | | | |
|---|---|---|---|---|---|
| | $C_2$ (%) ethylene | $C_4$ (%) butenes | $C_3$ (%) propene | $C_5$ (%) pentenes | $C_6$ (%) hexenes |
| 0 | 55 | 45 | 0 | 0 | 0 |
| 0.25 | 39.28 | 30 | 30 | 0.64 | 0.04 |
| 0.75 | 28.58 | 24.68 | 45.93 | 0.7 | 0.1 |
| 1.25 | 24.1 | 21.8 | 52.07 | 1.13 | 0.15 |
| 2 | 21.78 | 20.71 | 56.05 | 1.27 | 0.17 |

EXAMPLE 10

Regeneration under Hydrogen of the Catalyst W/Al-3 in a Dynamic Reactor

After having operated as in example 8, the catalyst (W/Al-3) is regenerated in a dynamic reactor under a stream of hydrogen (4 ml/min, 0.1 MPa) at 150° C. for 15 h. The catalyst, thus regenerated, then regains its activity in the metathesis of propene.

It should be clearly understood that the invention defined by the appended claims is not limited to the specific embodiments indicated in the above description but encompasses the alternative forms thereof which depart neither from the scope nor from the spirit of the present invention.

The invention claimed is:

1. A process for the metathesis of one or more reactants comprising a linear or branched hydrocarbon chain comprising an olefinic double bond $Csp^2$=$Csp^2$, in which this reactant or these reactants is/are reacted in the presence of a supported metal compound comprising a support based on aluminum oxide to which a tungsten hydride is grafted.

2. The process as claimed in claim 1, in which the reactant or reactants each comprise(s) from 2 to 30 carbon atoms.

3. The process as claimed in claim 1, in which the reactant is an unsaturated, linear or branched, acyclic hydrocarbon, comprising a $Csp^2$=$Csp^2$ double bond between two carbon atoms, of empirical formula $C_nH_{2n}$, n being an integer ranging from 2 to 30.

4. The process as claimed in claim 1, in which ethylene and butene are reacted to produce propylene.

5. The process as claimed in claim 1, in which the compound corresponds to the formula $R_1R_2C$=$CR_3R_4$ in which identical or different $R_i$ (i=1 to 4) substituents are chosen from hydrogen atoms, saturated, linear or branched, hydrocarbon groups and saturated cyclic hydrocarbon groups which optionally carry hydrocarbon substituents and which can be connected to the $Csp^2$ carbon of the olefinic double bond either directly or via a saturated hydrocarbon chain.

6. The process as claimed in claim 1, in which the compound corresponds to the formula $R_1R_2C$=$CR_3R_4$ in which identical or different $R_i$ (i=1 to 4) substituents are chosen from hydrogen atoms, saturated, linear or branched, hydrocarbon groups and aromatic rings which optionally carry saturated hydrocarbon substituents and which can be connected to the $Csp^2$ carbon of the olefinic double bond either directly or via a saturated hydrocarbon chain.

7. The process as claimed in claim 1, in which the degree of oxidation of the tungsten has a value chosen within a range extending from 2 to 6.

8. The process as claimed in claim 1, in which the tungsten atom is bonded to one or more hydrogen atoms and optionally to one or more hydrocarbon radicals R.

9. The process as claimed in claim 8, in which the hydrocarbon radicals R are identical or different, saturated or unsaturated, hydrocarbon radicals comprising from 1 to 20 carbon atoms and optionally comprising silicon.

10. The process as claimed in claim 1, in which the tungsten hydride is grafted to the support based on aluminum oxide according to the following scheme:

in which W, Al, O and H respectively represent tungsten, aluminum, oxygen and hydrogen atoms, M represents an atom of one or more elements of another oxide, R represents a hydrocarbon radical and x, y, w and z are integers, the sum (w+x+y+z) of which is equal to 2 to 6, and with x=1 to 3, y=1 to 5, w=0 to 4 and z=0 to 2, the —(Al—O) and —(M—O) bonds representing one or more single or multiple bonds respectively connecting the aluminum atom and the atom M to one of the atomic constituents of the support based on aluminum oxide, in particular to one of the oxygen atoms of this support.

11. The process as claimed claim 1, in which the support is chosen from supports homogeneous in composition based on aluminum oxide and from heterogeneous supports based on aluminum oxide comprising aluminum oxide essentially at the surface of said heterogeneous supports.

12. The process as claimed in claim 1, in which the support comprises aluminum oxide, mixed aluminum oxides or modified aluminum oxides.

13. The process as claimed in claim 1, in which the reaction is carried out at a temperature ranging from 20 to 600° C.

14. The process as claimed in claim 1, in which the reaction is carried out under an absolute pressure ranging from 0.01 to 8 MPa.

15. The process as claimed in claim 1, in which the metal compound is regenerated in the presence of hydrogen.

16. The process as claimed in claim 15, in which the regeneration is carried out at a temperature of between 50 and 300° C.

17. The process as claimed in claim 15, in which the regeneration is carried out with a hydrogen pressure ranging from 0.01 to 10 MPa.

18. The process as claimed in claim 7, wherein the range extends from 4 to 6.

19. The process as claimed in claim 9, wherein the hydrocarbon radicals comprise 1 to 10 carbon atoms.

20. The process as claimed in claim 13, wherein the temperature ranges from 20 to 350° C.

21. The process as claimed in claim 13, wherein the temperature ranges from 50 to 300° C.

22. The process as claimed in claim 13, wherein the temperature ranges from 80 to 200° C.

23. The process as claimed in claim 14, wherein the absolute pressure ranges from 0.01 MPa to 1 MPa.

24. The process as claimed in claim 14, wherein the absolute pressure ranges from 0.1 MPa to 0.5 MPa.

25. The process as claimed in claim 16, wherein the temperature is between 80 and 200° C.

26. The process as claimed in claim 17, wherein the hydrogen pressure ranges from 0.1 to 2 MPa.

* * * * *